(12) United States Patent
Tan (10) Patent No.: US 9,522,015 B2
(45) Date of Patent: Dec. 20, 2016

(54) FIXING DEVICE FOR AURAL HEMATOMA TREATMENT

(71) Applicant: Ta-Lun Tan, Taipei (TW)

(72) Inventor: Ta-Lun Tan, Taipei (TW)

( * ) Notice: Subject to any disclaimer, the term of this patent is extended or adjusted under 35 U.S.C. 154(b) by 152 days.

(21) Appl. No.: 14/071,177

(22) Filed: Nov. 4, 2013

(65) Prior Publication Data

US 2014/0128898 A1 May 8, 2014

(30) Foreign Application Priority Data

Nov. 2, 2012 (TW) .............................. 101140758 A (51) Int. Cl.
*A61B 17/34* (2006.01)
*A61B 17/3205* (2006.01)
*A61B 5/15* (2006.01)
*A61B 17/064* (2006.01)

(52) U.S. Cl.
CPC ......... *A61B 17/3205* (2013.01); *A61B 5/1411* (2013.01); *A61B 17/0643* (2013.01); *A61B 2017/0646* (2013.01)

(58) Field of Classification Search
CPC ................ A44C 7/001–7/004; A61B 17/0643; A61B 2017/0646; A61B 5/1411; A61B 5/15142; A61B 5/15186; A61B 5/15146; A61B 17/32093; A61B 17/3205

USPC ........... 606/117, 167, 188, 181, 182; 63/12; 40/300, 301, 303; 600/573–583
See application file for complete search history.

(56) References Cited

U.S. PATENT DOCUMENTS

| | | | | |
|---|---|---|---|---|
| 3,500,829 A | * | 3/1970 | Abramowitz | A44C 7/001 206/363 |
| 3,943,935 A | * | 3/1976 | Cameron | 606/188 |
| 4,696,119 A | * | 9/1987 | Howe et al. | 40/301 |
| 5,827,212 A | * | 10/1998 | Gaskill | 602/53 |
| 6,385,877 B1 | * | 5/2002 | Wikan | 40/301 |
| 2003/0121188 A1 | * | 7/2003 | Haar | A01K 11/001 40/301 |
| 2008/0221533 A1 | * | 9/2008 | Matityahu | A44C 15/0095 604/290 |
| 2011/0288574 A1 | * | 11/2011 | Curry | A61B 5/157 606/185 |

* cited by examiner

*Primary Examiner* — David C Eastwood
*Assistant Examiner* — Mikail Mannan
(74) *Attorney, Agent, or Firm* — Osha Liang LLP (57) ABSTRACT

A fixing device applicable to an ear including a cartilage and a skin covering the cartilage is provided. A gap is formed between the skin and the cartilage. The fixing device includes a puncturing unit and a clamping unit. The puncturing unit includes a puncturing needle penetrating the skin, the gap and the cartilage. The clamping unit includes a clamping opening engaged with the puncturing needle to have the puncturing unit and the clamping unit pressing the skin. Wherein, the skin is attached to the cartilage through the pressing of the puncturing unit and the clamping unit so as to remove the gap. In addition, the puncturing needle has a trench to drain the blood away.

3 Claims, 7 Drawing Sheets

FIXING DEVICE FOR AURAL HEMATOMA TREATMENT

CROSS-REFERENCE TO RELATED PATENT APPLICATION

The application claims priority to and the benefit of, pursuant to 35 U.S.C. §119(a), Taiwan Patent application No. 101140758, filed Nov. 2, 2012, entitled "FIXING DEVICE FOR AURAL HEMATOMA TREATMENT," by Ta-Lun Tan, the disclosure of which is incorporated herein in their entirety by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates to a fixing device, and more particularly to a fixing device with a puncturing unit and a clamping unit to fix the skin on the ear cartilage conformally.

BACKGROUND OF THE INVENTION

The ear is an organ with the pinna (or auricle in humans) external to the body. In the daily life of human and animals (the word "animals" is referred to include human in the following paragraphs), the ear might be damaged during running, jumping or doing other exercises to generate the symptom of hematoma because of the broken capillaries.

Generally, treatment of hematoma involves cutting the skin to drain the swelling and remove the blood clot as well as suturing the skin. The segregation of blood and blood clot will separate the skin and the ear cartilage to generate a gap between the skin and the ear cartilage even after removing the blood and the blood clot such that the symptom would be remained. Thus, in order to close the gap between the skin and the cartilage effectively, the skin should be forced to attach to the cartilage conformally. The traditional technology uses surgery sutures penetrating the skin and the cartilage to have the skin attached to the cartilage to speed up recovery of the wound.

Figure 1:
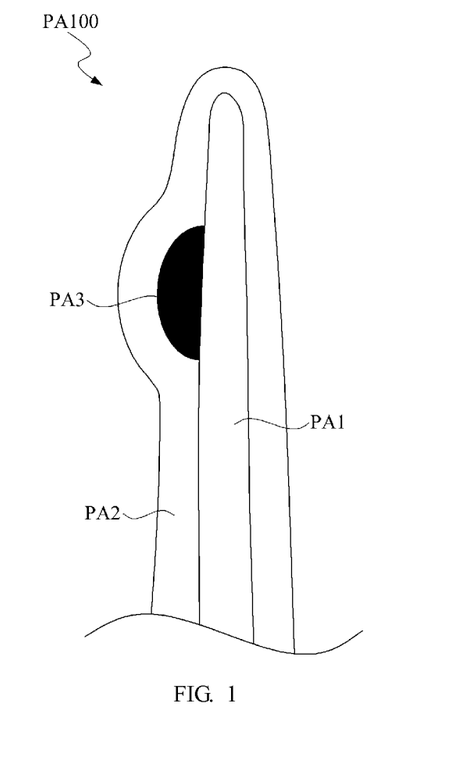
FIG. 1 is a cross-section view showing a ear with hematoma symptom.
Figure 2:
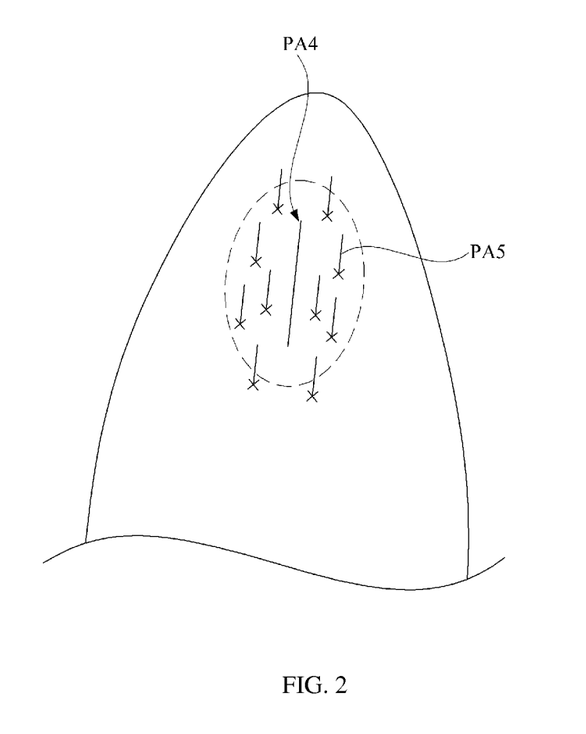
FIG. 2 is a top view showing the treatment of using the sutures to fix the skin to the cartilage.
Figure 3:
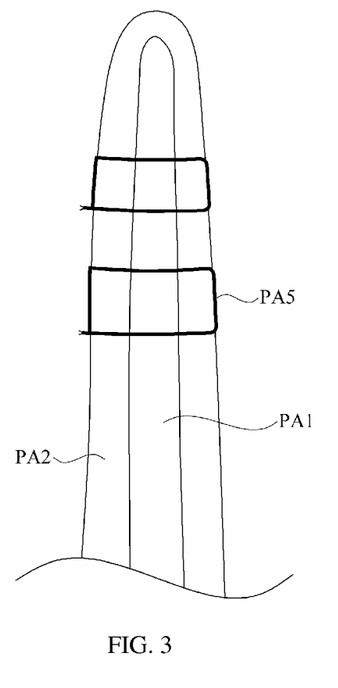
FIG. 3 is a cross-section view showing the treatment of using the sutures to fix the skin to the cartilage.

FIG. 1 is a cross-section view showing a ear with hematoma symptom. FIG. 2 is a top view showing the treatment of using the sutures to fix the skin to the cartilage. FIG. 3 is a cross-section view showing the treatment of using the sutures to fix the skin to the cartilage. As shown in FIG. 1, the ear PA100 has a cartilage PA1, a skin PA2, and a blood clot (or blood) PA3. The skin PA2 covers the cartilage PA1, and the blood clot PA3 is generated between the skin PA2 and the cartilage PA1. The skin PA2 deforms due to the pressure from the blood clot PA3. Thus, when the blood clot PA3 is removed through the cut PA4 on the skin PA2, a gap would be formed at the position where the blood clot PA3 is generated between the skin PA2 and the cartilage PA1.

Referring to FIG. 2 and FIG. 3, the traditional treatment uses sutures PA5 to penetrate the skin PA2 and the cartilage PA1 back and forth and then tie the knots on the sutures PA5 to fix the deformed skin PA2 on the cartilage PA1 so as to close the wound between the skin PA2 and the cartilage PA1. To have the deformed region of the skin PA2 with a certain area uniformly attached to the cartilage PA1, it is needed to use lots of sutures PA5 which costs lots of effort and time.

Accordingly, it is demanded to develop a new fixing mechanism, which can fix skin on the cartilage rapidly so as to enhance operating convenience and also save the time.

BRIEF SUMMARY OF INVENTION

As mentioned above, the traditional technology uses surgery sutures penetrating the skin and the cartilage to have the skin attached to the cartilage. However, the operation of sutures, which needs to penetrate the skin and cartilage back and forth and ties the knots, is complicated and needs to be highly concentrated, which will cost lots of effort and time.

Accordingly, it is a main object to provide a fixing device, which adopts a puncturing unit penetrating the skin and the cartilage, and uses a clamping unit to engage with the puncturing unit such that the skin would be attached to the cartilage conformally through the pressing of the puncturing unit and the clamping unit. It is another object to provide a puncturing unit, which adopts a trench on a puncturing needle to drain the blood of the hematoma.

In one aspect, a fixing device is provided in accordance with an embodiment of the present invention. The fixing device is applicable to an ear including a cartilage and a skin covering the cartilage, and a gap filled of blood is formed between the skin and the cartilage. The fixing device comprises a puncturing unit and a clamping unit. The puncturing unit includes at least one puncturing needle configured to penetrate the skin, the gap and the cartilage to drain the blood in the gap. The clamping unit includes at least one clamping opening configured to be engaged with the puncturing needle to have the puncturing unit and the clamping unit pressing the skin. Wherein, the skin is attached to the cartilage through the pressing of the puncturing unit and the clamping unit so as to remove the gap.

According to an embodiment of the present invention, the clamping unit further comprises an attaching portion. The attaching portion includes an attaching surface and a holding surface, and the clamping opening is formed on the attaching surface. As an embodiment, the clamping unit further comprises a holding portion located on the holding surface for a user to hold the clamping unit. In addition, the clamping unit further comprises a gasket, located on the attaching surface, and the gasket has a through hole connected to the clamping opening.

According to an embodiment of the present invention, the puncturing unit further comprises a pressing portion, the pressing portion includes an attaching surface and a pressing surface, the puncturing needle is located on the attaching surface, and the pressing surface is utilized for a user to press the puncturing unit. As a preferred embodiment, the puncturing unit further comprises a gasket, located on the attaching surface, and the puncturing needle penetrates the gasket. In addition, the pressing portion is circle-shaped or polygon-shaped.

According to an embodiment of the present invention, the puncturing needle has a trench for draining the blood in the gap.

In another aspect, an apparatus for treating aural hematoma is provided in accordance with an embodiment of the present invention. The apparatus includes a fixing device, which is applicable to an ear including a cartilage and a skin covering the cartilage, and a gap filled of blood is formed between the skin and the cartilage. The fixing device comprises a puncturing unit and a clamping unit. The puncturing unit includes at least one puncturing needle configured to penetrate the skin, the gap and the cartilage to drain the blood in the gap. The clamping unit includes at least one clamping opening configured to be engaged with the puncturing needle to have the puncturing unit and the clamping unit pressing the skin. Wherein, the skin is attached to the cartilage through the pressing of the puncturing unit and the clamping unit so as to remove the gap.

According to an embodiment of the present invention, the clamping unit further comprises an attaching portion. The attaching portion includes an attaching surface and a holding surface, and the clamping opening is formed on the attaching surface. As an embodiment, the clamping unit further comprises a holding portion located on the holding surface for a user to hold the clamping unit. In addition, the clamping unit further comprises a gasket, located on the attaching surface, and the gasket has a through hole connected to the clamping opening.

According to an embodiment of the present invention, the puncturing unit further comprises a pressing portion, the pressing portion includes an attaching surface and a pressing surface, the puncturing needle is located on the attaching surface, and the pressing surface is utilized for a user to press the puncturing unit. As a preferred embodiment, the puncturing unit further comprises a gasket, located on the attaching surface, and the puncturing needle penetrates the gasket. In addition, the pressing portion is circle-shaped or polygon-shaped.

According to an embodiment of the present invention, the puncturing needle has a trench for draining the blood in the gap.

In a further aspect, a method of treating aural hematoma is provided in accordance with an embodiment of the present invention. The method includes: puncturing a gap filled of blood in an ear with a puncturing unit, wherein the ear comprises a cartilage and a skin covering the cartilage, and the gap is formed between the skin and the cartilage, wherein the puncturing needle comprises at least one puncturing needle to penetrate the skin, the gap and the cartilage to drain the blood in the gap; and fixing a clamping unit to the puncturing unit such that the clamping unit and the puncturing unit press the skin to attach the skin to the cartilage so as to remove the gap, wherein the clamping unit comprises at least one clamping opening engaged with the puncturing needle.

According to an embodiment of the present invention, the clamping unit further comprises an attaching portion having an attaching surface, and a gasket located on the attaching surface, wherein the clamping opening is formed on the attaching surface, and the gasket has a through hole connected to the clamping opening.

According to an embodiment of the present invention, the puncturing unit further comprises an attaching surface and a gasket located on the attaching surface, wherein the puncturing needle is located on the attaching surface, and the gasket is penetrated by the puncturing needle.

According to an embodiment of the present invention, the puncturing needle has a trench thereon for draining the blood in the gap.

As mentioned above, in compared with the traditional technology, which uses sutures to fix the skin and the cartilage, the fixing device provided in the present invention featuring a puncturing unit with a puncturing needle penetrating the skin and the cartilage and a clamping unit engaging with the puncturing needle to have the puncturing unit and the clamping unit pressing the skin on the both side of the ear so as to have the skin attached to the cartilage. The operation would not waste the user too much effort and time to attach the skin to the cartilage, and thus greatly enhance operational convenience and efficiency.

The embodiments adopted in the present invention would be further discussed by using the flowing paragraph and the figures for a better understanding.

BRIEF DESCRIPTION OF THE DRAWINGS

The present disclosure will become more fully understood from the detailed description and the accompanying drawings, wherein.

DETAILED DESCRIPTION OF THE INVENTION

The following description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. For purposes of clarity, the same reference numbers will be used in the drawings to identify similar elements. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

Figure 4:
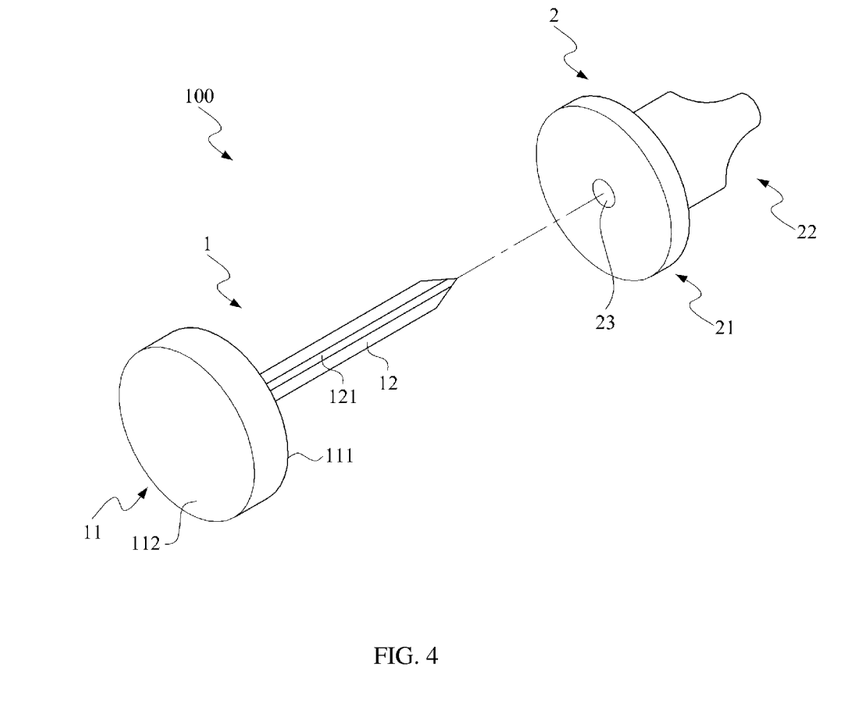
FIG. 4 is a 3D schematic view of the fixing device in accordance with a first embodiment of the present invention.
Figure 5:
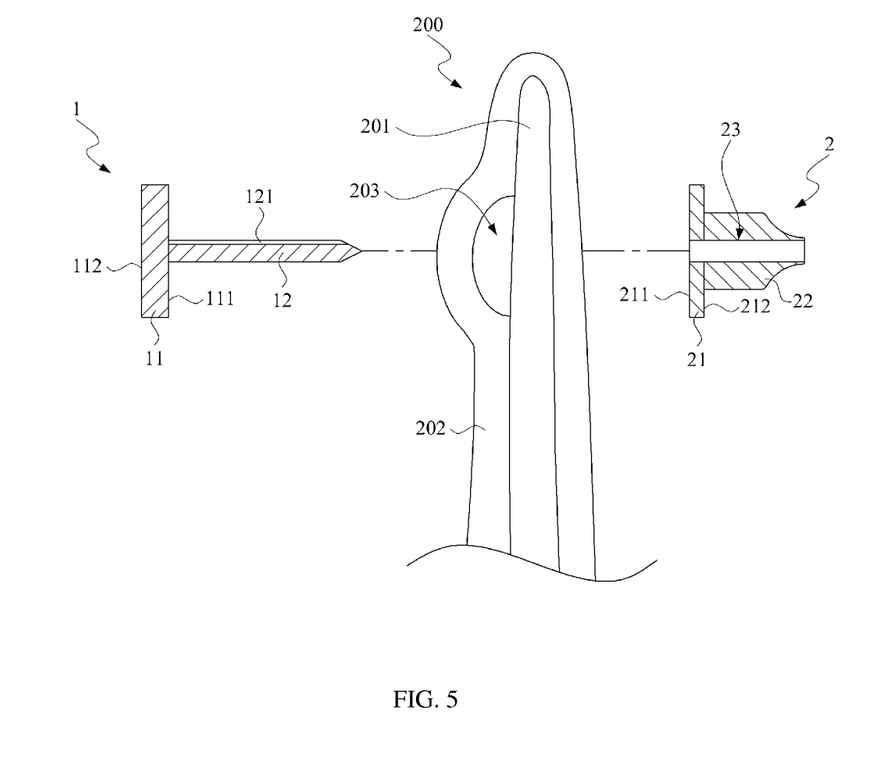
FIG. 5 is an explosive view of the fixing device arranged on the ear.
Figure 6:
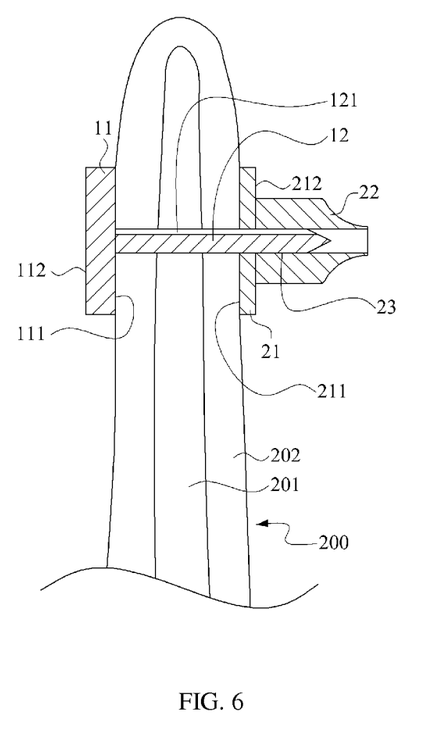
FIG. 6 is a cross-section view showing the fixing device and the ear.

FIG. 4 is a 3D schematic view of the fixing device in accordance with a first embodiment of the present invention, FIG. 5 is an explosive view of the fixing device arranged on the ear, and FIG. 6 is a cross-section view showing the fixing device and the ear. As shown in FIG. 4 and FIG. 5, the fixing device 100 includes a puncturing unit 1 and a clamping unit 2. The fixing device 100 is applicable to an ear 200 having a cartilage 201 and a skin 202 covering the cartilage 201. In addition, there is a gap 203 between the skin 202 and the cartilage 201. In practice, the gap 203 would be filled with blood if the ear 200 showing the hematoma symptom.

The puncturing unit 1 includes a pressing portion 11 and a puncturing needle 121. The pressing portion 11 has an attaching surface 111 and a pressing surface 112 on the opposite sides thereof. The pressing portion 11 may be circle-shaped or polygon-shaped, such as triangle-shaped or square-shaped. The attaching surface 111 is utilized to contact the skin 202 of the ear 200, and the pressing surface 112 allows the user to press the puncturing unit 1. The puncturing needle 12 is located on the attaching surface 111 and penetrates the skin 202, the gap 203 and the cartilage 201. The puncturing needle 12 also has a trench 121, which is capable to drain the blood in the gap 201 away when the puncturing needle 12 is penetrating the skin 202, the gap 203, and the cartilage 201.

The clamping unit 2 includes an attaching portion 21, a holding portion 22, and a clamping opening 23. The attaching portion 21 includes an attaching surface 211 and a holding surface 212 on the opposite sides thereof. The attaching surface 211 is utilized to contact the skin 202 of the ear 200. The holding portion 22 is located on the holding surface 212 to allow the user to hold the clamping unit 2. The clamping opening 23 is formed on the attaching surface 211 to engage with and fix the puncturing needle 12 so as to have the puncturing unit 1 and the clamping unit 2 pressing the skin 202 and have the skin 202 attached to the cartilage 201.

Referring to FIG. 5 and FIG. 6, the puncturing unit 1 features the puncturing needle 12 penetrating the skin 202, the gap 203, and the cartilage 201 to have the attaching surface 111 pressing the skin 202, and the clamping unit 2 features the clamping opening 23, which is capable to engage with and fix the puncturing needle 12, to have the attaching surface 211 pressing the skin 202. In addition, the blood filled in the gap 203 would be drained through the trench 121 on the puncturing needle 12 outside the ear 200. Thus, the skin 202 is pressed toward the cartilage 201 through the pressing force applied by the puncturing unit 1 and the clamping unit 2 so as to remove the gap 203 to have the skin 202 attached to the cartilage 201 conformally.

Figure 7:
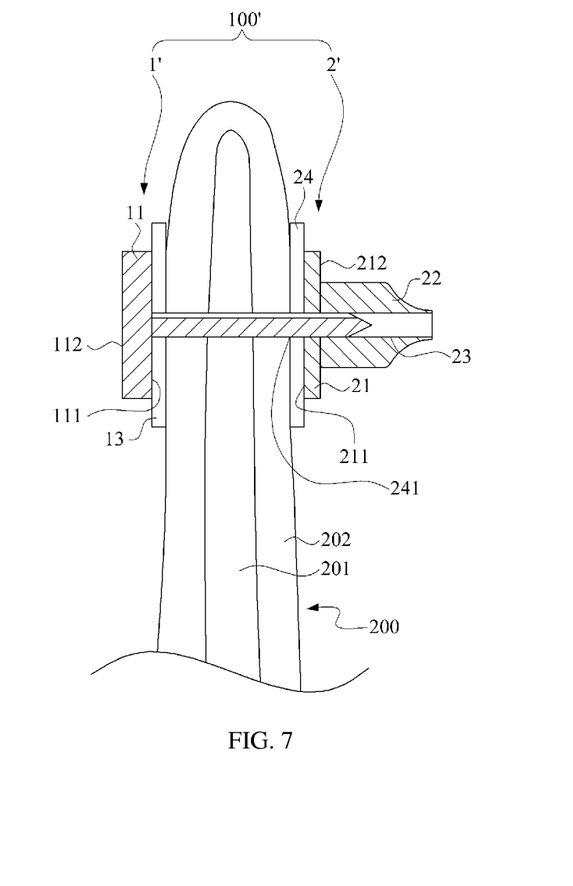
FIG. 7 is a cross-section view showing a fixing device in accordance with a second embodiment of the present invention.

FIG. 7 is a cross-section view showing a fixing device in accordance with a second embodiment of the present invention. As shown, the fixing device 100' includes a puncturing unit 1' and a clamping unit 2'. Comparing the fixing device 100' of the present embodiment and the fixing device 100 of the first embodiment, the puncturing unit 1' of the present embodiment further has a gasket 13 and the clamping unit 2' further has a gasket 24 also. The gasket 13 of the puncturing unit 1' is located right on the attaching surface 111 and the puncturing needle 12 penetrates the gasket 13. The gasket 24 of the clamping unit 2' is located on the attaching surface 211 and has a through hole 241 connected to the clamping opening 23. The gaskets 13 and 24 might be composed of elastic materials, such as silicone, which is capable to ease the stress between the puncturing unit 1' and the clamping unit 2'. In addition, the size of the gaskets 13 and 24 for pressing the skin 202 can be adjusted according to the area size of the deformed region on the skin 202 of the ear 200.

It is believed that people of ordinary skilled in the art would be able to understand that by using the fixing device of the present invention, after using the puncturing needle to drain the blood in the ear with hematoma symptom away, the user can use the clamping unit to engage with the puncturing needle penetrating the skin and the cartilage so as to have the skin attached to the cartilage rapidly. Thus, in compared with the transitional technology using the sutures to fix the skin to the cartilage, the fixing device of the present invention can save the cost of time and effort and is very easy to use.

In addition, a major application of the present invention is the surgery for the animals with damaged ear, by using the fixing device of the present invention to attach the skin on the cartilage, the time needed for the surgery can be significantly reduced to ease the tension and uncomfortable feeling due to the surgery.

The detail description of the aforementioned preferred embodiments is for clarifying the feature and the spirit of the present invention. The present invention should not be limited by any of the exemplary embodiments described herein, but should be defined only in accordance with the following claims and their equivalents. Specifically, those skilled in the art should appreciate that they can readily use the disclosed conception and specific embodiments as a basis for designing or modifying other structures for carrying out the same purposes of the present invention without departing from the scope of the invention as defined by the appended claims.

What is claimed is:

1. A method of treating aural hematoma, comprising:
puncturing a gap filled of blood in an ear with a puncturing unit, wherein the ear comprises a cartilage and a skin covering the cartilage, and the gap is formed between the skin and the cartilage, wherein the puncturing unit comprises at least one puncturing needle to penetrate the skin, the gap and the cartilage to drain the blood in the gap, wherein the puncturing needle has a trench thereon for draining the blood in the gap;
fixing a clamping unit to the puncturing unit such that the clamping unit and the puncturing unit press the skin to attach the skin to the cartilage so as to remove the gap, wherein the clamping unit comprises at least one clamping opening engaged with the puncturing needle.

2. The method of claim 1, wherein the clamping unit further comprises an attaching portion having an attaching surface, and a gasket located on the attaching surface, wherein the clamping opening is formed on the attaching surface, and the gasket has a through hole connected to the clamping opening.

3. The method of claim 1, wherein the puncturing unit further comprises an attaching surface and a gasket located on the attaching surface, wherein the puncturing needle is located on the attaching surface, and the gasket is penetrated by the puncturing needle.

\* \* \* \* \*